(12) United States Patent
Nilsson (10) Patent No.: US 6,671,161 B2
(45) Date of Patent: Dec. 30, 2003

(54) REMOVING DOSE ELECTRIC CHARGE

(75) Inventor: Thomas Nilsson, Mariefred (SE)

(73) Assignee: Microdrug AG, Hergiswil (CH)

(*) Notice: Subject to any disclaimer, the term of this patent is extended or adjusted under 35 U.S.C. 154(b) by 69 days.

(21) Appl. No.: 09/928,444

(22) Filed: Aug. 14, 2001

(65) Prior Publication Data

US 2003/0011957 A1 Jan. 16, 2003

(30) Foreign Application Priority Data

Jul. 13, 2001 (SE) .............................................. 0102522

(51) Int. Cl.$^7$ .................................................. H05F 3/00
(52) U.S. Cl. ..................................... 361/212; 361/213
(58) Field of Search ................................ 361/212, 213, 361/221, 226

(56) References Cited

U.S. PATENT DOCUMENTS

| 3,743,540 | A | * | 7/1973 | Hudson | 134/1 |
|---|---|---|---|---|---|
| 3,807,853 | A | * | 4/1974 | Hudson | 355/15 |
| 4,096,543 | A | * | 6/1978 | Kozuka et al. | 361/230 |
| 4,329,694 | A | * | 5/1982 | Edwards et al. | 346/74.3 |
| 4,355,884 | A | * | 10/1982 | Honda et al. | 355/14 CH |
| 4,514,779 | A | * | 4/1985 | Wilkinson | 361/213 |
| 5,400,208 | A | * | 3/1995 | Pazda et al. | 361/221 |
| 5,566,042 | A | * | 10/1996 | Perkins et al. | 361/228 |
| 5,949,635 | A | * | 9/1999 | Botez | 361/213 |
| 5,960,609 | A | * | 10/1999 | Abrams et al. | 53/428 |

* cited by examiner

*Primary Examiner*—Gregory Toatley, Jr.
*Assistant Examiner*—Z Kitov
(74) *Attorney, Agent, or Firm*—Young & Thompson (57) ABSTRACT

A method and a device for quick neutralization of a created electrostatic field formed by a multitude of basically charged particles includes a medication powder (180) deposited onto a defined target area (160) of a substrate member (140) in the course of a dose forming process. A charge generator emits charges, which are directed towards the target area of the substrate member such that the electric field created by the accumulated charges from the deposited particles is neutralized by the added charges. Various elements may be used to generate neutralizing charges, but an ion source (195) is most efficient in achieving neutralization of the dose charge and the substrate. The source may be applied so that the dose (180) and the target area (160) are exposed to the emitted charges during the entire or part of the dose forming process.

26 Claims, 11 Drawing Sheets

REMOVING DOSE ELECTRIC CHARGE

TECHNICAL FIELD

The present invention relates to a method and a device for quick neutralization of a created electrostatic field formed by a multitude of basically charged particles comprising a medication powder deposited onto a defined target area of a substrate member in a process of forming a pre-metered dose suitable for inhalation.

BACKGROUND

The dosing of drugs is carried out in a number of different ways in the medical service today. Within health care there is a rapidly growing interest in the possibility of dosing medication drugs as a powder directly to the airways and lungs of a patient by means of an inhaler in order to obtain an effective, quick and user-friendly administration of such substances.

A dry powder inhaler, DPI, represents a device intended for administration of powder into the deep or upper lung airways by oral inhalation. A deep lung deposition is desirable for systemic delivery of medication drugs, but for local treatment of the airways, the objective is local deposition, not deep lung. With deep lung should be understood the peripheral lung and alveoli, where direct transport of active substance to the blood can take place. In order for a particle to reach into the deep lung the aerodynamic particle size should typically be less than 3 $\mu$m, and for a local lung delivery typically less than 5 $\mu$m. Larger particle sizes will easily stick in the mouth and throat, which underlines the importance of keeping the particle size distribution of the dose within tight limits to ensure that a high percentage of the dose actually is deposited in the deep lung upon inhalation when the objective is systemic delivery of a drug. Furthermore, the inspiration must take place in a calm manner to decrease air speed and thereby reduce deposition in the upper respiratory tracts.

To succeed with systemic delivery of medication powders to the deep lung by inhalation there are some criteria, which have to be fulfilled. It is for instance very important to obtain a high dosing accuracy in each administration to the user. A very high degree of de-agglomeration of the medication powder is also of great importance. This is not possible with dry powder inhalers of today without special arrangements as for example a so-called spacer.

Powders for inhalers have a tendency of agglomerating, in other words to clod or to form smaller or larger lumps, which then have to be de-agglomerated. De-agglomeration is defined as breaking up agglomerated powder by introducing electrical, mechanical, or aerodynamic energy. Usually de-agglomeration is performed in at least two stages: stage one is in the process of depositing powder while building up the dose and stage two is in the process of dispersing the powder during the patient's inspiration of air through the DPI.

The term electro-powder refers to a finely divided medication powder presenting controlled electric properties being suitable for administration by means of an inhaler device. Such an electro-powder provides possibilities for a better dosing from equipment using a technique for electric field control such as disclosed in our U.S. Pat. No. 6,089,227 as well as our Swedish Patents No. 9802648-7 and 9802649-5, which present excellent inhalation dosing performance. The state of the art also discloses a number of solutions for depositing powder for dosing. The International Application WO 00/22722 presents an electrostatic sensing chuck using area matched electrodes. U.S. Pat. No. 6,063,194 discloses a powder deposition apparatus for depositing grains on a substrate using an electrostatic chuck having one or more collection zones and using an optical detection for quantifying the amount of grains deposited. U.S. Pat. No. 5,714,007 and U.S. Pat. No. 6,007,630 disclose an apparatus for electrostatically depositing a medication powder upon predefined regions of a substrate, the substrates being used to fabricate suppositories, inhalants, tablet capsules and the like. In U.S. Pat. No. 5,699,649 and U.S. Pat. No. 5,960,609 are presented metering and packaging methods and devices for pharmaceuticals and drugs, the methods using electrostatic photo technology to package microgram quantities of fine powders in discrete capsule and tablet form.

A common difficulty encountered when using electrostatic technology and/or electrical fields in combination with electrostatic charging of the powder particles in a deposition process, is to neutralize the created electrostatic field formed by the multitude of deposited particles and the charge of the substrate, if an isolator, as the particles are being deposited on the substrate for forming the dose. If the neutralization of charges is incomplete or takes too long it will affect the forming of the dose negatively in that the charged particles already deposited will present a local repelling electric field, which tends to stop newly attracted particles from settling on the targeted area of the substrate and forces newcomers to settle at the outskirts of the target area. The repelling field grows in strength as more particles are deposited on the target area. Finally, the field is so strong that further deposition is not possible even if the net field strength at some distance from the target area is exerting an attractive force on the charged particles.

In cases where electrostatic chucks are used, regardless of whether the chuck substrate, normally of a dielectric material, is pre-charged in the deposition area or areas to create the necessary local electric field in the target area(s), or a system of electrodes are used to attract the charged particles or if a combination of pre-charging and electrodes are used, it is always difficult to fill the target area with the correct amount of particles, because the repelling field grows stronger with every particle deposited, leading to a spreading out of particles over a larger area than the intended target area. This is also true where the target areas, the deposition areas, constitute beads, which are captured and held by the chuck by for instance electrostatic forces during the deposition of particles onto the beads themselves. It is thus often impossible to form doses of sufficient mass and suitable spatial shape. Often, the chuck principle also requires powders of predetermined or known specific charge ($\mu$C/g) in order to predict the mass of particles attracted to the chuck, which by itself presents a big challenge.

Further, prior art technology devices seldom reach a sufficiently high degree of de-agglomeration, and an exact dose with a low relative standard deviation (RSD) between doses is not well controlled. This is partly due to difficulties in controlling the production line parameters during production of the doses, partly to shortcomings in the design of the inhaler device, which make it hard to comply with regulatory demands. The difficulties leave much to be desired when it comes to dose conformity and lung deposition effectiveness of the medication substance. Therefore, there is still a demand for pre-fabricated high accuracy pre-metered doses to be loaded into an inhaler device, which then will ensure repeated and exact systemic or local pulmonary delivery of doses administered by inhalation.

SUMMARY

A method and a device are defined for quick neutralization of a created electrostatic field formed by a multitude of basically charged particles comprising a medication powder deposited onto a defined target area of a substrate member in the course of a dose forming process.

A source of charges or a charge generator, not to be confused with the particle generator, is arranged such that the emitted charges, positive or negative or both, are directed towards the target area of the substrate member so that the electric field created by the accumulating charges from a multitude of particles is neutralized by the added charges. Various means, e.g. corona, induction or tribo effect may be used to generate equalizing charges, but in a preferred embodiment, an ion source has been found to be most efficient in achieving neutralization of the dose charge and the substrate. The chosen method or device is selected not to affect the powder substance in any other way but to neutralize the electric charges.

The source is applied so that the dose and the target area are exposed to the emitted charges during the whole or part of the dose forming process. Alternatively, the source may be positioned out of range of the target area such that the substrate member with the target area or even the source itself is repositioned by a servo device when a neutralization of accumulated charge in the dose is needed. For best results, it is necessary to choose a source of suitable strength and provide adequate screening to direct the charges towards the dose or, if the target area is larger than the area where the dose is formed, towards the part of the dose where the deposition is taking place.

Figure 3:
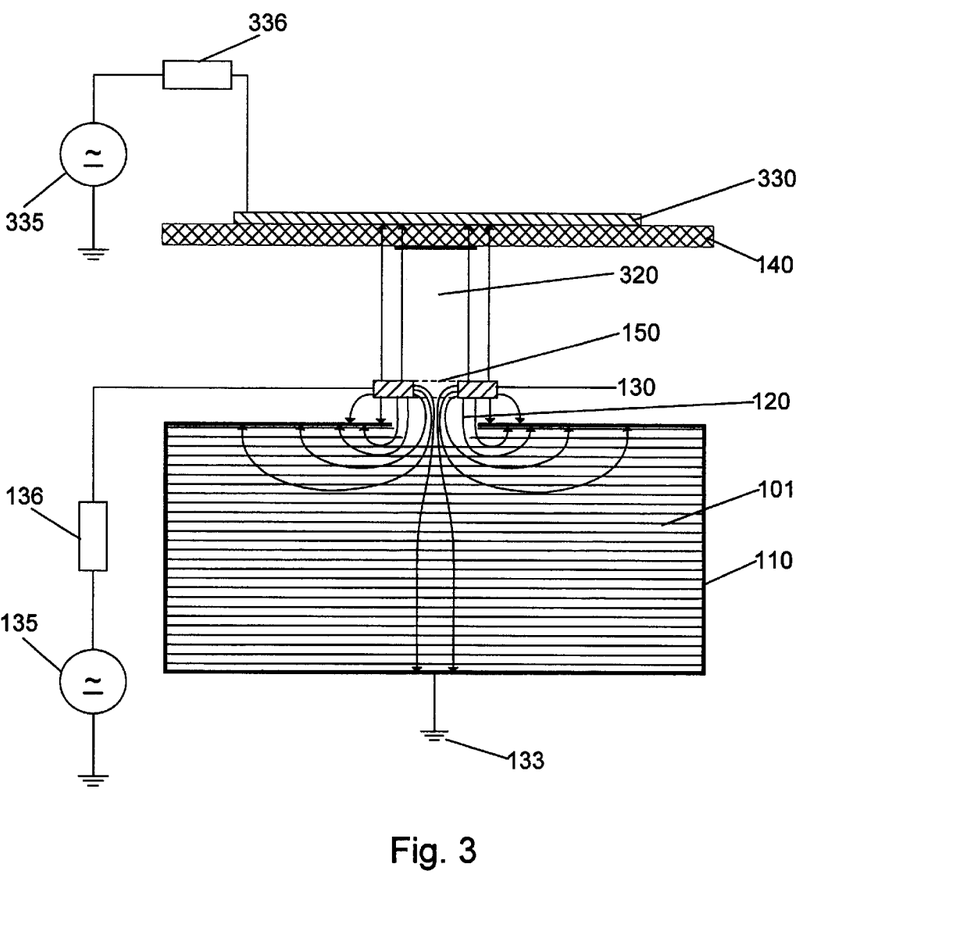

Making electric contact with the electrode behind the target area on the substrate member is sometimes difficult because of the physical requirements put on the substrate member by the servo device and control system. Restrictions may exist in terms of acceptable materials, physical implementations etc, which make standard methods of making electric contact difficult or impossible to use. The present invention provides a non-contact electric connection by using yet a further ion source, put behind the substrate member. The ion source ionizes the gas, normally air, between the electrode and the servo device controlling the movements of the substrate member. Then, if a voltage source is arranged feeding the ion source chassis with an appropriate voltage the voltage also will appear as a potential on the electrode, without too much voltage loss. In this manner the electrode is included in the circuit and will work as intended in attracting powder particles to the target area.

BRIEF DESCRIPTION OF THE DRAWINGS

The invention, together with further objects and advantages thereof, may best be understood by referring to the following detailed description taken together with the accompanying drawings, in which:

FIG. 1 illustrates in principle how the deposition of charged particles onto the target area of the substrate member is made more and more difficult and erratic because of the increasing repelling electric field created by the accumulated charge of the multitude of already deposited particles;

FIG. 2 illustrates in principle a first embodiment of an iris diaphragm/shutter comprising one electrode only, showing how charged particles are being transferred from the particle generator to the target area of the substrate member;

FIG. 3 illustrates the same embodiment as in FIG. 2 but with the transfer of particles inhibited by a repelling acting electric field from the electrode of the iris diaphragm/shutter;

FIG. 4 illustrates in principle a second embodiment of an iris diaphragm/shutter comprising two electrodes, showing how charged particles are transferred from the particle generator to the target area of the substrate member;

FIG. 5 illustrates a typical embodiment of an iris diaphragm/shutter comprising two electrodes;

FIG. 6 illustrates in principle a third embodiment of an iris diaphragm comprising four electrodes, showing how charged particles are transferred from the particle generator to the target area of the substrate member, which may be moved by a servo mechanism during dose forming;

FIG. 7 illustrates in principle one side of a typical iris diaphragm showing a second electrode;

FIG. 8 illustrates in principle one side of a typical iris diaphragm showing a first electrode;

FIG. 9 illustrates in principle an iris diaphragm with two electrodes, a dose being formed onto the target area of the substrate member and two ion sources for removing accumulated charge in the dose being formed;

FIG. 10 illustrates in principle an iris diaphragm with two electrodes, a dose being formed onto the target area of the substrate member, a servo arrangement for moving the substrate member in relation to the iris and an ion source for removing accumulated charge in the dose being formed;

FIG. 11 illustrates, taken together with FIG. 10, in principle a substrate member in the shape of a revolving cassette with more than one target area, doses being formed onto the target areas and an ion source for removing—one by one—accumulated charges in the doses being formed; and FIG. 12 illustrates schematically a substrate member, an iris diaphragm, a dose in forming and an ion source positioned behind the substrate member connecting without physical contact the third voltage source with the third electrode.

DESCRIPTION OF THE INVENTION

A method and a device involving a source of charges are disclosed for quick neutralization of a created electrostatic field formed by a multitude of charged particles of a medication powder deposited onto a defined target area of a substrate member in the course of a dose forming process. Spatial distribution of particles onto the target area or dose bed is achieved by means of electro-dynamic field technique applied to the distribution and deposition of particles in a dose forming process. The term "electro-dynamic field technique" in the context of this document refers to the effective electric field in four dimensions, space and time, resulting from well controlled—in terms of timing, frequency and amplitude—potentials applied to a number of electrodes placed in suitable positions in the space confined by a dose forming apparatus. The term "quasi-stationary electric field" is in this context used to describe an electric field or fields being controlled by voltage source devices with controlled impedance, all part of a control system, where the applied voltages may be controlled arbitrarily and individually in the low-frequency time-domain.

To facilitate the understanding of where and how voltages are applied all voltages are assumed to be referenced to ground potential throughout this document. Naturally, ground potential may be exchanged for an arbitrary potential when utilizing the invention and it will be apparent to a person skilled in the art that any singular potential or voltage may be referenced to another potential or voltage source, e.g. in order to simplify or improve a control system, without departing from the spirit and scope of the invention as defined in the appended claims.

A powder particle generator is provided, which either produces positively and/or negatively charged powder particles by corona-, tribo- or induction-charging. The charged particles are emitted from the generator into a controlled atmosphere, normally air, where they enter an electric field coming from suitably positioned electrodes at suitable potentials supplied by controlled voltages from suitable voltage sources. At least one of the electrodes comprises an electric iris diaphragm/shutter. The iris diaphragm/shutter has at least one aperture of suitable size and shape where particles can pass through and it is positioned between the particle generator and the substrate. In a typical embodiment, the iris diaphragm comprises two electrodes with a thin isolating wafer member between them, and a single aperture through the iris diaphragm. The electrodes and the isolating wafer member are typically made as a printed circuit board (PCB) with topside and bottom side. The electrode (topside by definition) closest to the substrate member is typically circular in shape and concentric with the aperture, while the other electrode (bottom side by definition) is closest to the particle generator and may cover the lower side of the PCB completely. In a preferred embodiment, the substrate member is positioned upside down above the particle generator such that the net electrostatic force acting on emitted charged particles is directed upwards counteracting the force of gravity during forming of the dose. In this manner no big or heavy particles can land on the target area by accident under the influence of gravity alone. The potentials applied to the electrodes of the iris diaphragm are controlled by a control system, which is not part of the invention. The potentials are preferably varied in a determined way during the course of the dose forming process such that the dose obtains the intended properties. While the transfer of particles takes place from the generator through the iris diaphragm to the target area of the substrate member the potential fed to the top electrode of the iris is typically a few hundred volts, positive or negative, in order to attract charged particles. The electrode on the bottom side is typically fed with a potential between zero and some tens of volts in order to slightly repel the charged particles and help guiding particles through the iris diaphragm. The particles emerging from the aperture topside of the iris diaphragm enter the attracting field emanating from the electrode behind the target area of the substrate member. The attracting electrode is typically fed with a potential between 500 and 2000 V. The emerging particles therefore continue on their path in the direction of the target area. During the dose forming process the transfer of particles may be interrupted by the control system, which may create a strong repelling electric field within the iris diaphragm by feeding suitable opposing potentials to the electrodes such that no charged particles can penetrate the aperture of the iris diaphragm.

In order to eliminate the prior art limitations in total dose mass and poor spatial control of the dose layout it is essential to achieve fast and efficient neutralization of charges from the charged powder particles and from the target area of the substrate, i.e. the dose bed, thus eliminating the repelling electric field from the dose during forming. Various methods, e.g. corona, induction or tribo effect may be used to generate equalizing charges, but in a preferred embodiment very quick neutralization is achieved e.g. by arranging a source of positively charged helium ions, so called alpha-particles, near the substrate such that the emitted ions are directed towards the dose and the target area of the substrate. The emitted ions ionize the air and the resulting oxygen and nitrogen ions of both positive and negative charge may be attracted to the dose and the substrate, whereby some of them will hit the dose and the substrate and recombine, neutralizing the accumulated charges in the process. For best results, it is of course necessary to choose an ion source of suitable strength and provide adequate screening to direct the charges towards the dose or, if the target area is larger than the area where the dose is formed, towards the part of the dose where the deposition is taking place.

By immediate, i.e. within a fraction of a second, neutralization of the particle charge once the particle has been deposited on the substrate the negative influence from the particle charge on incoming particles is eliminated. The spatial deposition of the particles is thus vastly improved with no particles settling outside the target area, because the sum of charges on the dose bed and in the dose being formed as a whole is continuously removed in this way eliminating a distorting, repelling electric field from arising. In a typical embodiment of the invention the accumulated charge within the dose and dose bed is regularly removed during the dose forming process as described. If the ion source cannot be positioned and screened to add neutralizing charges directly to the dose and the target area, the dose may be brought within the range of an ion source by a servo device or vice versa, such that the accumulated charge is neutralized at least once and more preferably several times during the forming of the dose. It is also typical that the substrate member must pass by the ion source to neutralize any residual charge from the target area before commencing a dose forming operation.

The electro-powder forms an active dry powder substance or dry powder medication formulation with a fine particle fraction (FPF) presenting of the order 50% or more of the powder mass with an aerodynamic particle size below 5 $\mu$m and provides electrostatic properties with an absolute specific charge per unit mass of the order 0.1 to 25 $\mu$C/g after charging, and presents a charge decay rate constant $Q_{50}$ of more than 0.1 s, a tap density of less than 0.8 g/ml and a water activity $a_w$ of less than 0.5.

As an illustrative example the dose forming process may best be understood by taking reference in FIG. 2. The particle generator 110, not to be confused with the mentioned ion source, emits particles 101 provided with a positive or negative charge by corona-, tribo- or induction-charging, whereupon the particles enter an imposed first electric field 120. The type of charge of the particles depends on the powder characteristics, method of charging and materials in the generator so that the majority of the particles are charged either negatively or positively when they are emitted from the generator to take part in the dose forming process. In the following discussion and in the illustrations it is assumed that the emitted particles are positively charged. However, this depends on the properties of the powder and the generator and it is equally possible that the particles are negatively charged, in which case the applied potentials must change signs, but the discussion is still valid. In order to control the dose forming process in terms of total dose mass and dose forming time, the transfer of charged particles from the particle generator to the target area of the substrate member must be controlled. To this end, a first electric field is applied between ground 133 and a first electrode 130 connected to a first voltage source 135, including source impedance 136. The electrode is preferably positioned a short distance in the range 0.5–25 mm from the substrate member 140 between the particle generator 110 and the substrate member 140. The strength and direction of the created electric field 120 may be adjusted by adjusting the potential of the electrode within wide limits from a negative to a positive voltage, as set by the voltage source. Charged particles are thereby either attracted to (see FIG. 2)

or repelled from (see FIG. 3) the first electrode, which has at least one aperture 150 of suitable size and shape where charged particles can pass through. Such apertures may be circular, elliptic, square or narrow slits or any other shape in order to suit the dose forming process. In a preferred embodiment, the aperture or apertures are in the range 50–5000 μm as main measures. However, particles attracted by the first electrode easily stick to it, which impairs the efficiency of the system and frequent cleaning may become necessary.

Figure 4:
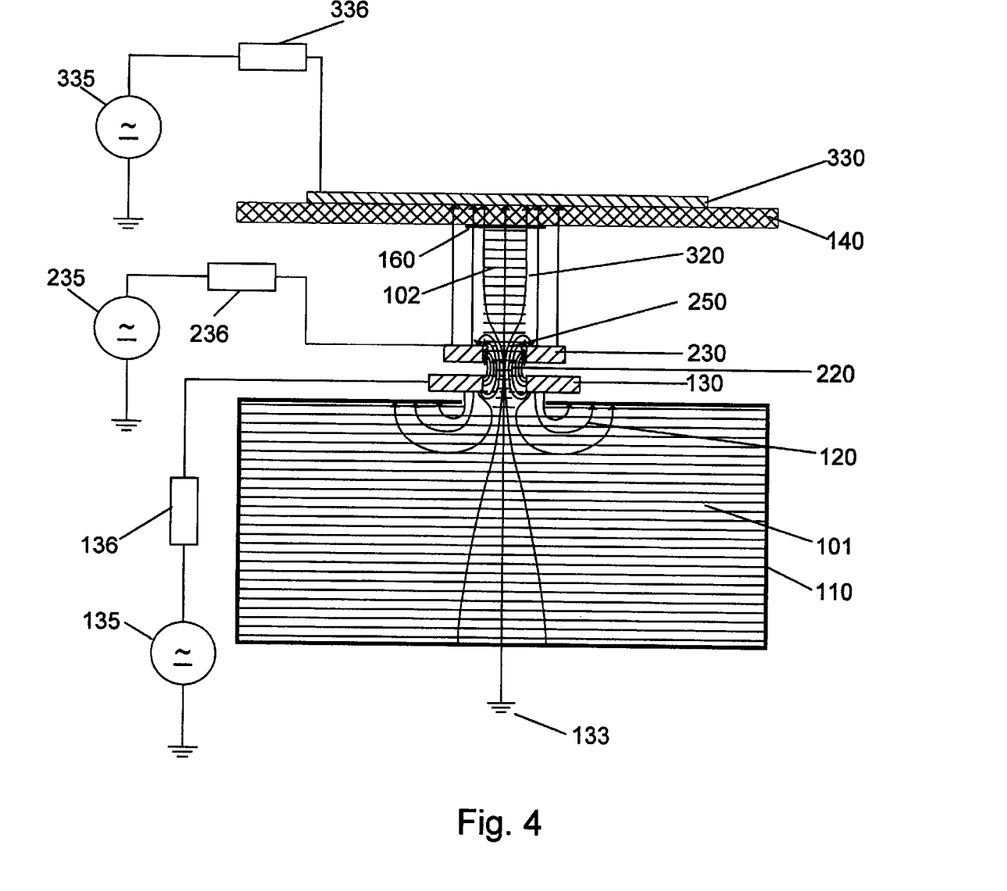
Figure 5:
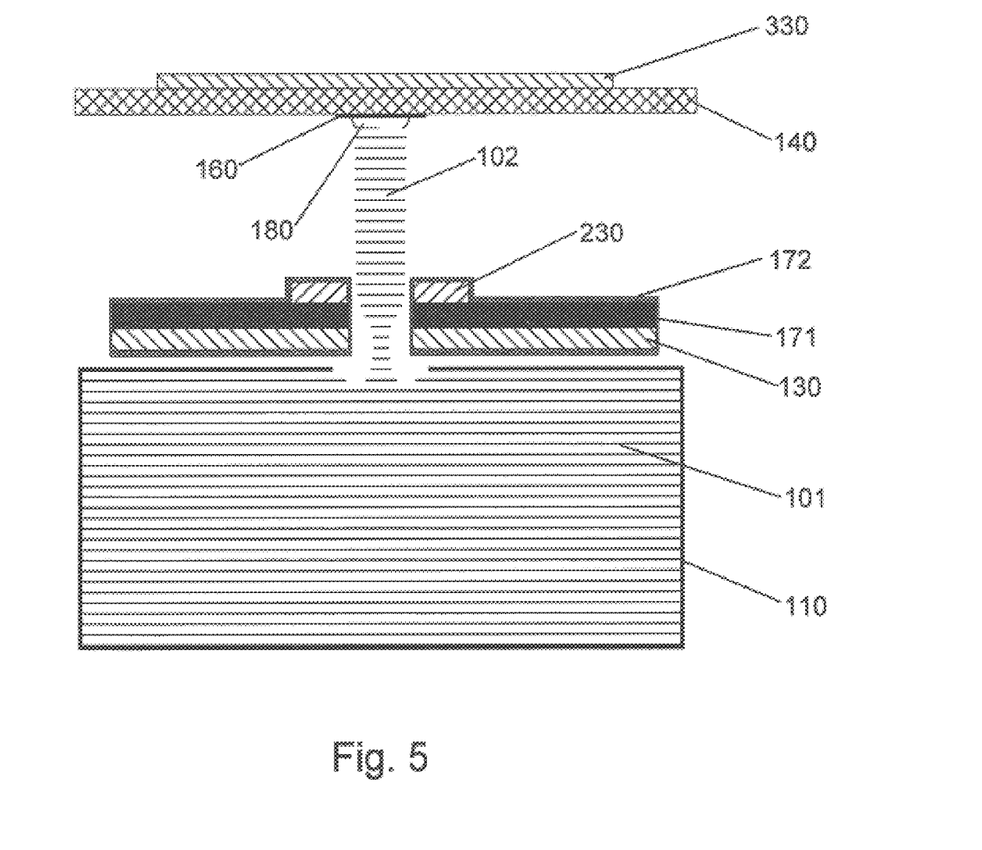

To eliminate the sticking effect and further improve the level of control of the transfer of particles to the target area of the substrate member, an optional second electrode 230 as illustrated in FIG. 4, may be introduced. It should be positioned in a plane parallel to the first electrode 130, in between the first electrode and the substrate at a distance between 0.07 and 2.5 mm from the first electrode. In a preferred embodiment, illustrated in FIG. 5, the first and second electrodes are integrated in an isolating wafer member 171 between the electrodes. The outward faces of the electrodes are preferably coated with an isolating coating 172 of a few microns in thickness, e.g. parylene, to stop possible short-circuiting of electrodes by sticking particles. The thickness of the wafer is typically in the range 0.07–2 mm. As an illustrative example the electrodes and the wafer member may be made as a printed circuit board. There are many types commercially available, e.g. in terms of number of possible conductor layers, physical flexibility and thickness.

The wafer member 171 constitutes a physical barrier between the particle generator 110 and the substrate 140 with the dose bed that is the target area 160 for the deposition of charged particles 102. The distance between the top electrode or electrodes on the top of the wafer member and the substrate is in the range 0.5 to 25 mm. The only possibility for the particles to reach the dose bed is therefore to go through the available apertures of the first and second electrodes and possible extra electrodes, if introduced.

A further third electric field 320 is set up between ground 133 and a third electrode 330 connected to a third voltage source 335. It is possible to reference the third voltage source to the output of the first or second electrode instead of ground to simplify control of the deposition process. The third electrode is preferably positioned in close proximity behind the substrate member 140 and the dose bed 160, such that the electric field lines go through the dose bed in the direction of the particle generator 110. The substrate member may be made of a dielectric or semi-conductive material or even a conducting material or a combination of different such materials. In the case when the material in the dose bed is conductive, the dose bed may constitute the third electrode. The strength and direction of an ensuing third electric field 320 may be adjusted by adjusting the potential of the third electrode within wide limits from a negative to a positive voltage as set by the third voltage source, if connected to the electrode, such that the charged particles are either transported towards or away from the third electrode.

Figure 6:
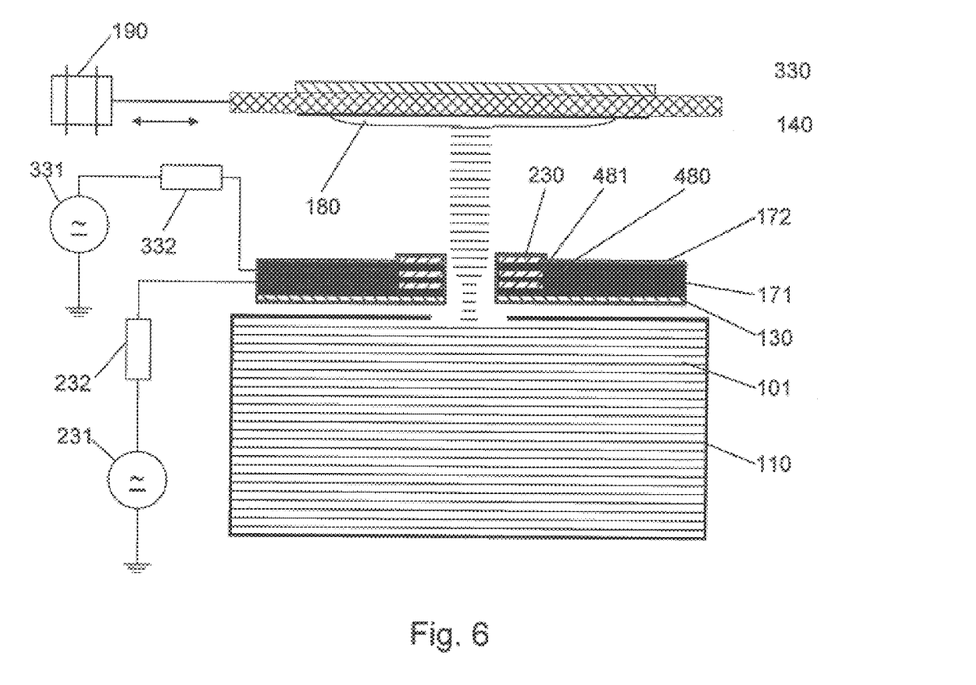
Figure 7:
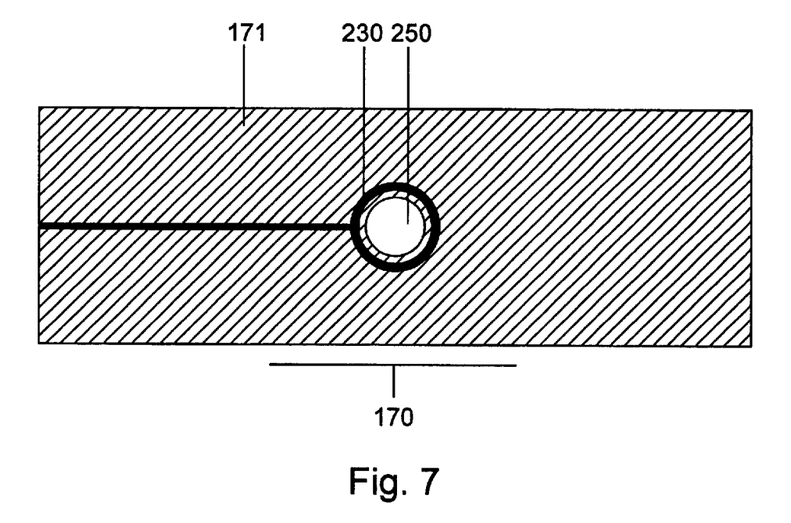
Figure 8:
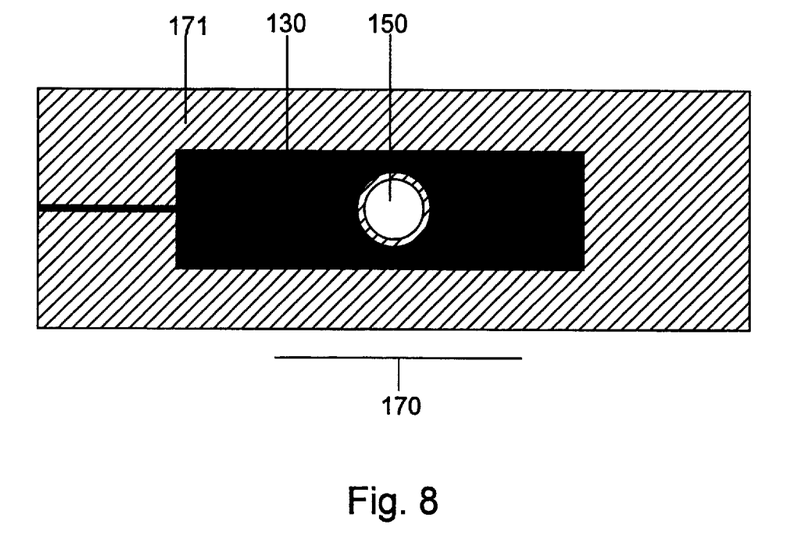

Charged particles 101 emitted from the generator 110 enter the combined electric field resulting from the potentials applied to the first, second and third electrodes respectively. The first electrode alone acts as an electric iris diaphragm device 170 and the addition of the optional second electrode improves the efficiency of the device considerably. A typical embodiment of the electric iris diaphragm is illustrated in FIGS. 7 and 8, showing the topside and bottom side respectively. The at least one electrode, constituting the iris diaphragm, transfers charged powder particles 101, emitted from the generator, to the target area 160 on the substrate member in a controlled orderly way in terms of mass, direction and speed, like a printer ink-jet. After passing the iris diaphragm 170, the particles are accelerated in the third electric field, which may have an AC component, in the direction of the target area of the substrate member, i.e. the dose bed 160, under the attractive field force caused by the third field emanating from the third electrode behind the dose bed. The bed may be stationary or moving during the distribution of the particles. By utilizing a servomechanism 190, schematically illustrated in FIG. 6, the deposition of the particles can be controlled such that the spatial distribution of the particles on the dose bed area can be controlled arbitrarily.

In order to avoid that particles are deposited at random inside or even outside the target area, because of the local repelling electric field emanating from charges of already deposited particles, the created electrostatic field must be neutralized during the dose forming process. In that case, no significant local repelling electric fields will build up, which may distort the third electric field and weaken its attractive power, leading to a scattering of incoming charged particles. If charges accumulating in the dose and dose bed are frequently neutralized new particles will automatically go from the output of the iris diaphragm to the closest point of the dose bed such that there is a sharp distinction between the formed dose and the surrounding areas of the substrate.

Figure 1:
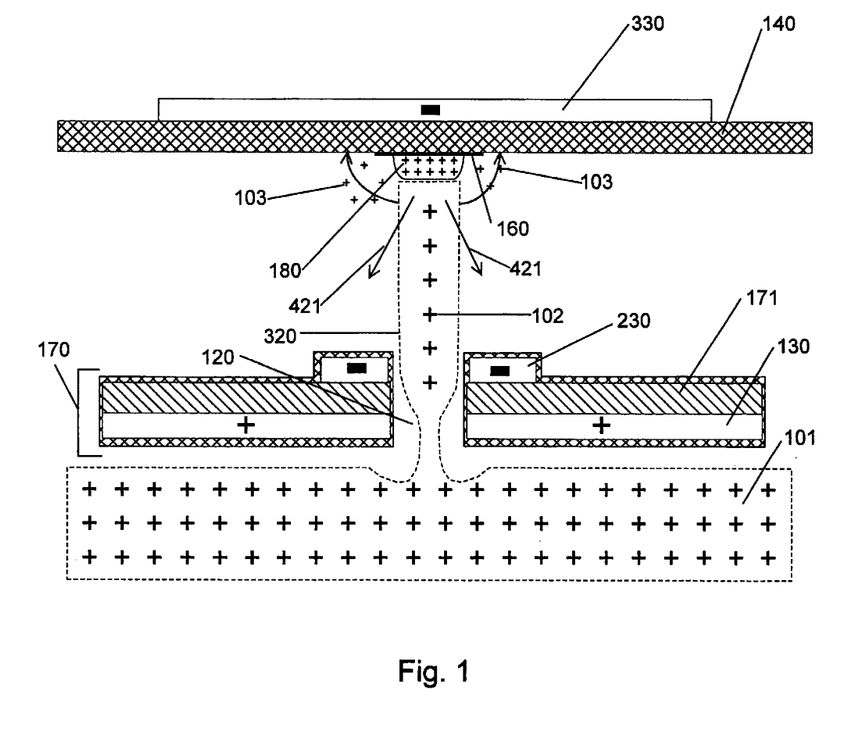
Figure 2:
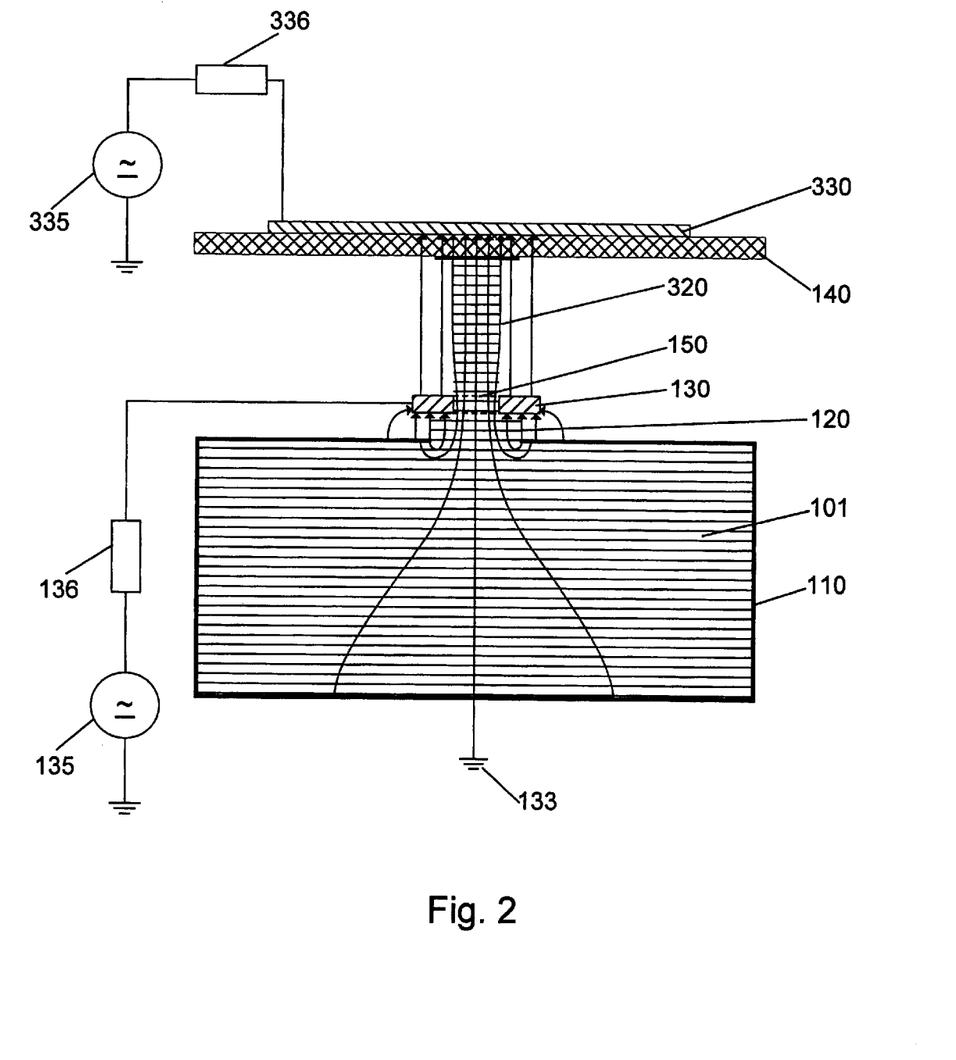

The problem presented by the created repelling field caused by the accumulated charged particles is illustrated in FIG. 1. Basically charged powder particles 101 (positive or negative, positive charge is assumed in FIG. 1) are transported by an electric field 120 through an iris diaphragm 170 and then by a field 320 towards the target area 160 of the substrate member 140, where the particles 102 are deposited forming the dose 180. The more particles that are deposited the less free area is available for new particles. The accumulated charged particles create a local electric field, which exerts a force 421, which in turn repels newcomers 102, forcing some 103 to settle outside the target area or to be retained and wasted on the walls of the dose forming apparatus. In a preferred embodiment, electro-powder is used, but other medication powders may be possible to use, which is easily recognized by people of ordinary skill in the art.

Figure 9:
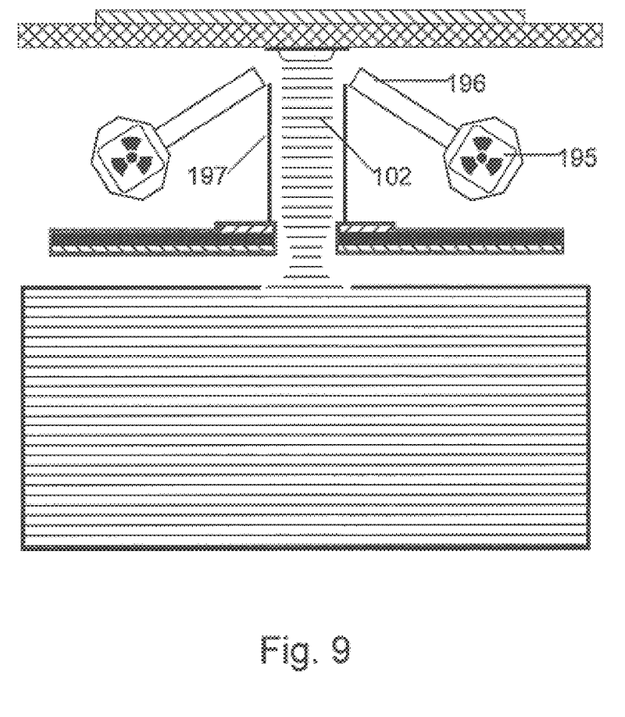
Figure 10:
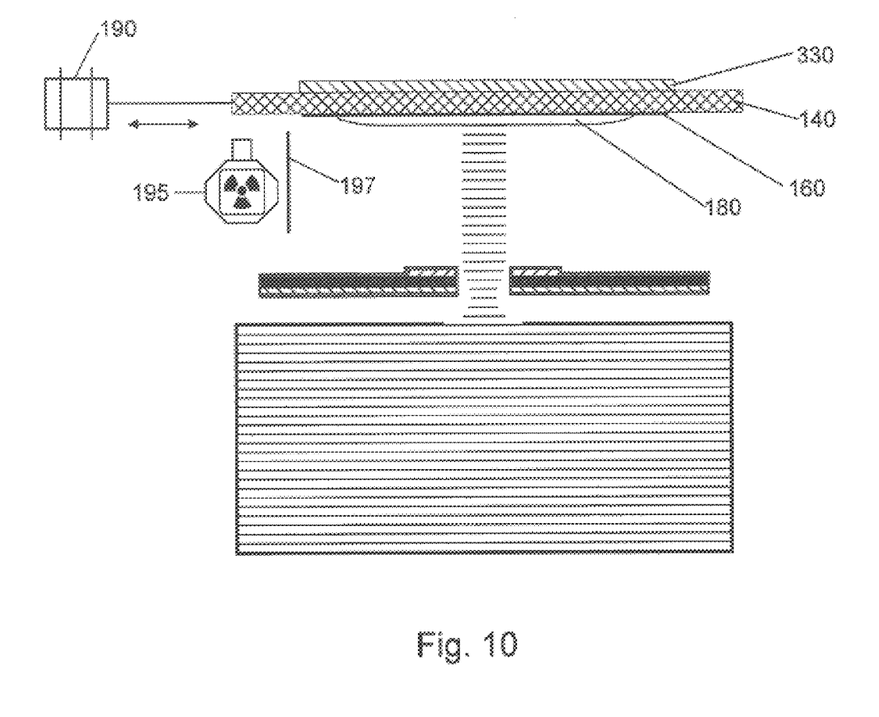
Figure 11:
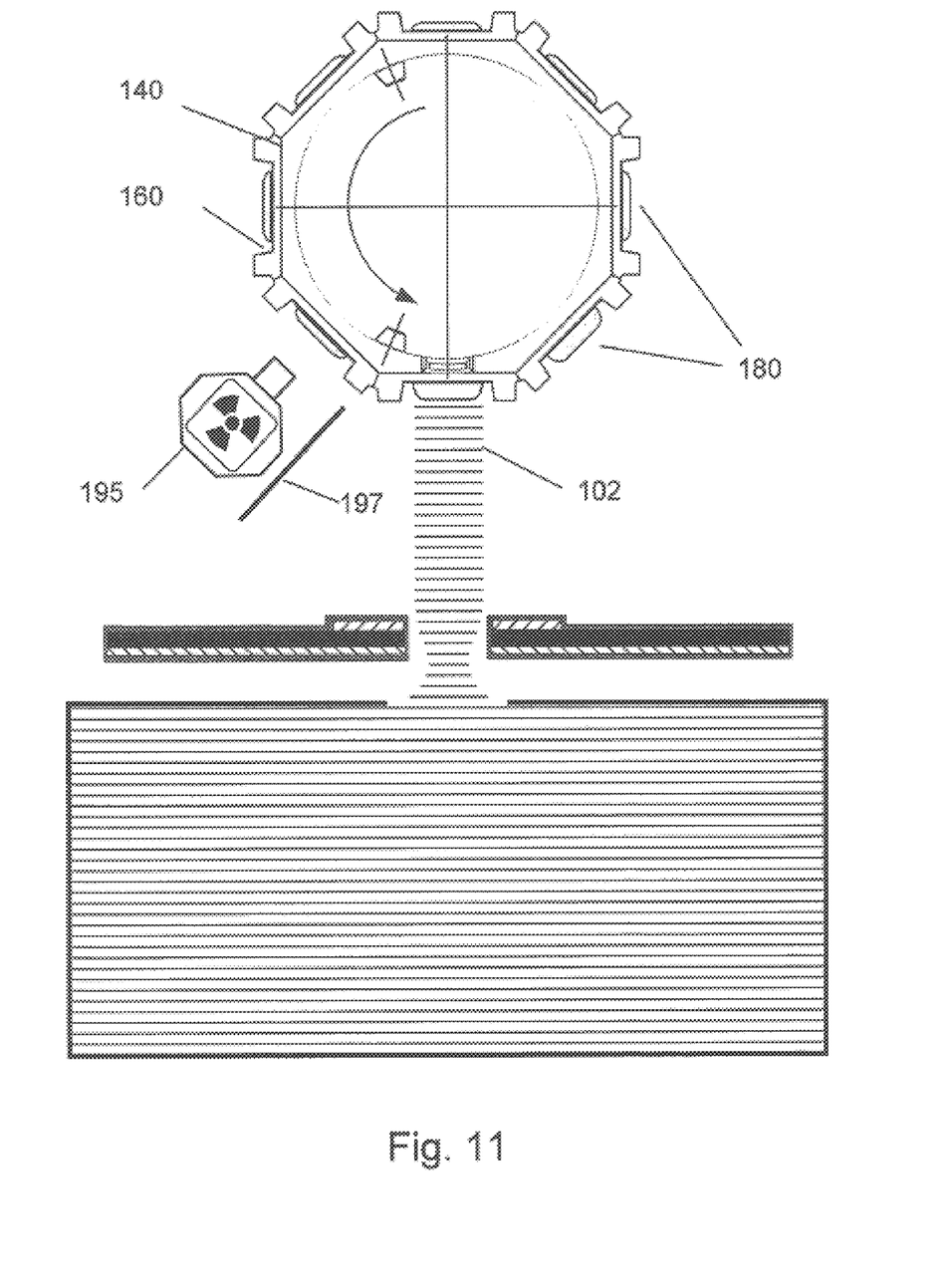
Figure 12:
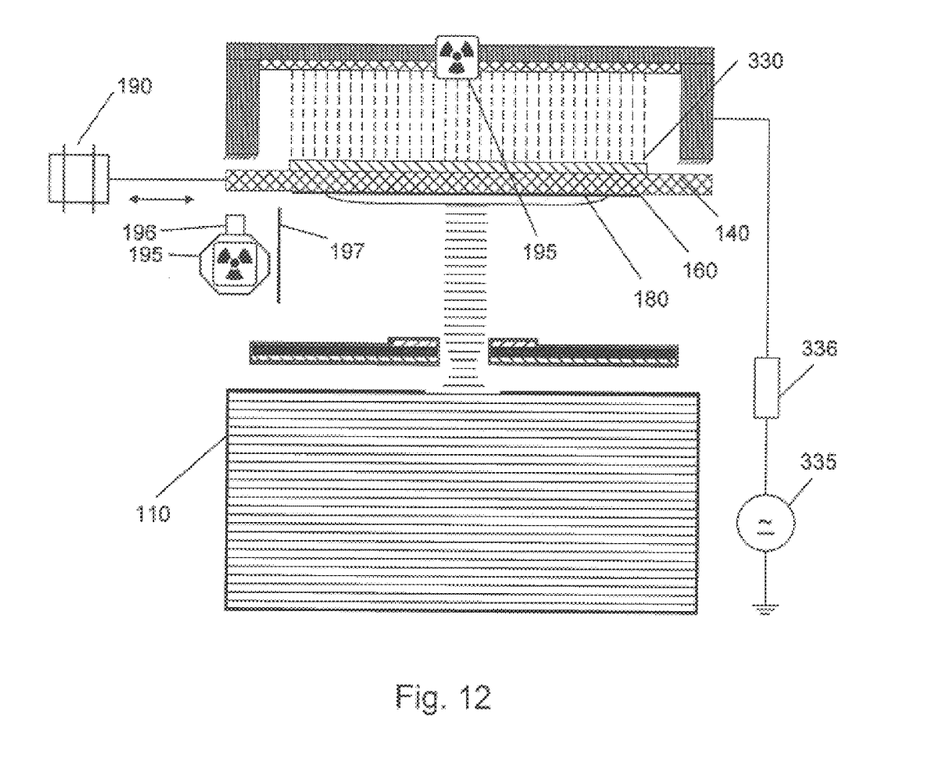

A key element of the invention is schematically illustrated in FIGS. 9, 10 and 11 i.e. the element neutralizing the accumulated charge of particles deposited on the dose bed. Various methods, e.g. corona, induction or tribo effect may be used to generate neutralizing charges, but in a preferred embodiment, a radioactive source 195 of alpha-particles (positively charged helium atoms) has been found to be most efficient. These sources are readily commercially available, e.g. from NRD LLC, Grand Island, N.Y. and are specifically used to discharge electrically charged objects. The alpha particles are scattered uniformly in all directions from, for instance, a point source and ionize the surrounding air creating both positive and negative ions. The new ions are attracted to oppositely charged particles and other charged objects in the vicinity and recombine to form regular atoms using the surplus charge of the objects with which they collide. The active range from the ion source is only a few centimeters. It is very easy to stop the alpha particles within the active range by putting any solid material in the way, like a sheet of paper. A preferred radioactive point source is model P-2042 Nuclespot™, which is based on Polonium-210, but other models are available to suit all kinds of applications. Polonium-210 is currently used and has a long record of use in all kinds of industry where static electricity is a problem. The radiation does not affect the medication powder in any way besides neutralizing the charge and it leaves no residue besides helium atoms (inert gas), which are the result of the alpha particles colliding with air molecules taking up two electrons from oxygen or nitrogen atoms. In their effort to recombine, a current of ions is established that quickly neutralizes charged objects and surfaces within the active range of the radioactive point source.

In one embodiment, illustrated in FIG. 9, it is possible to direct the alpha particles by designing at least one direction member 196 pointing to the spot on the dose bed where the powder particles 102 are deposited, such that immediately after the deposition the charge of the individual particles is neutralized. In a different embodiment, the ion source 195 is put outside the spot where the dose is formed, illustrated in FIG. 10. The previously mentioned servo device 190 is now set up to withdraw the substrate 140 with the dose bed 160 after only a partial dose forming operation before too many charged particles 102 have been deposited in order to neutralize the accumulated charges from the dose bed and the dose 180 by exposing the dose and substrate to the emitted ions from the source. Yet another embodiment is illustrated in FIG. 11, showing a typical arrangement where the substrate member is a cassette 140 carrying at least one target area 160 for dose forming and an ion source directed towards the target area, which will receive the next dosing in a repeated sequence of dose forming operations. Generally, for all embodiments it is necessary to include screens 197, which will absorb charges that otherwise risk interfering with charged particles being transported in the electric fields set up to control the transport, distribution and final deposition of the particles in the dose forming process.

In a different embodiment physical constraints may exist in a member carrying one or more substrate members intended for doses, which make it difficult or impossible to arrange a contacting of an electrode behind the substrate member necessary for creating the third electric field as previously discussed. In such case, illustrated schematically in FIG. 12, a separate ion source 195 may advantageously be applied to make electrical contact with the third electrode 330 behind the substrate member 140 without actual physical contact. The emitted alpha particles ionize the air, which acts as an electric conductor between the ion source and the third electrode, which must be electrically conductive. The ion source should be of suitable size and placed within its working range 0–30 mm from the third electrode on the backside of the substrate member. If the metal shell of the ion source is connected to the third voltage source 335 with effective internal impedance 336, which now includes the impedance of the air gap, part of the applied voltage will also be present as a potential on the third electrode, such that the third field can be fully controlled.

It is worth noting that for all practical embodiments of the invention depositing large amounts of powder is no problem, provided the negative influence of the created electrostatic field from the accumulated charged particles constituting the dose and of the stray charges of the substrate is neutralized by removing the charges as described in the foregoing description. Then, the field strength from the third electrode is approximately constant through the substrate and developing dose. The distribution process and the forming of the dose are not sensitive to variations between particles in total charge or specific charge. As long as a particle has a charge of the right type and manages to pass the screening in the iris diaphragm, it will automatically be deposited onto the dose bed as long as the field exists. Provided suitable measuring instruments are put to use for monitoring the dose while it is formed, it is easy to control the described dose forming process on-line, using standard prediction, feed-forward and feed-back control methods, in combination if necessary.

What has been said in the foregoing is by example only and many variations of the disclosed embodiments may be obvious to a person of ordinary skill in the art, without departing from the spirit and scope of the invention as defined by the appended claims.

What is claimed is:

1. A method for quick neutralization of a created electrostatic field formed by a multitude of basically charged particles comprising a medication powder deposited onto a defined target area of a substrate member in a dose forming process, comprising:

applying a device comprising a source of electric charges emitting positive or negative or both types of charges within range of a dose being formed onto said defined target area of said substrate member;

arranging a transmission of equalizing electric charges to a multitude of charged particles, deposited onto said defined target area of said substrate member, for the purpose of equalizing the charge in the dose being formed and also equalizing stray charges on the substrate surface, wherein said transmission of equalizing electric charges is applied to a partial dose of said medication powder prior to subsequent deposition of further medication powder to complete said dose.

2. The method according to claim 1, further comprising arranging an ion source as the source of equalizing electric charges, and providing said ion source with direction members and screens.

3. The method according to claim 1, further comprising arranging a corona type charge generator as said source of equalizing electric charges, and providing the ion source with direction members and screens.

4. The method according to claim 1, further comprising arranging an induction type charge generator as said source of equalizing electric charges, and providing the ion source with direction members and screens.

5. The method according to claim 1, further comprising arranging a tribo type charge generator as said source of equalizing electric charges, and providing the ion source with direction members and screens.

6. The method according to claim 1, further comprising arranging a continuous transmission of equalizing charges from a source of charges directed towards a multitude of charged particles deposited on the target area of the substrate member during a dose forming process.

7. The method according to claim 1, further comprising positioning a source of equalizing charges out of range of a dose forming area such that the substrate with said defined target area and the dose being formed can be brought within range of emitted charges by means of a servo device, such that the dose being formed is temporarily brought in a position to get its accumulated electrostatic field neutralized at least once during the forming of the dose.

8. A method for quick neutralization of a created electrostatic field formed by a multitude of basically charged particles comprising a medication powder deposited onto a defined target area of a substrate member in a dose forming process comprising:

establishing electric contact over an air gap between a non-contactable electrode behind a substrate member and a voltage source by using a source of electric charges emitting sufficient charges into said air gap to convey an electric potential between the electrode and the voltage source having an impedance, inclusive of said air gap, less than 1 GΩ;

connecting a controlled potential from the voltage source through the air gap to the electrode thus creating a necessary electric field emanating from the electrode for transportation of the charged particles to the target area in the dose forming process;

applying a device comprising a source of electric charges emitting positive or negative or both types of charges within range of a dose being formed onto said defined target area of said substrate member;

arranging a transmission of equalizing electric charges to a multitude of charged particles, deposited onto said defined target area of said substrate member, for the purpose of equalizing the charge in the dose being formed and also equalizing stray charges on the substrate surface, wherein said transmission of equalizing electric charges is applied to a partial dose of said medication powder prior to subsequent deposition of further medication powder to complete said dose.

9. The method according to claim 8, further comprising arranging an ion source as the source of equalizing electric charges, and providing said ion source with direction members and screens.

10. The method according to claim 8, further comprising arranging a corona type charge generator as said source of equalizing electric charges, and providing the ion source with direction members and screens.

11. The method according to claim 8, further comprising arranging an induction type charge generator as said source of equalizing electric charges, and providing the ion source with direction members and screens.

12. The method according to claim 8, further comprising arranging a tribo type charge generator as said source of equalizing electric charges, and providing the ion source with direction members and screens.

13. A device for quick neutralization of a created electrostatic field formed by a multitude of basically charged particles comprising a medication powder deposited on a defined target area of a substrate member in a dose forming process, wherein a source of electric neutralizing charges is emitting positive or negative or both types of charges within a working range of a medication dose being formed on the target area of the substrate member; and a mechanical arrangement transmitting charges from the source of electric charges into a multitude of charged particles deposited onto the target area of said substrate member for a purpose of neutralizing a charge of the dose in forming and stray charges on the substrate surface, wherein said transmission of neutralizing electric charges is applied to a partial dose of said medication powder prior to subsequent deposition of further medication powder to complete said dose.

14. The device according to claim 13, wherein said voltage source has an impedance less than 1 GΩ.

15. The device according to claim 13, wherein said source of neutralizing electric charges is an ion source which is provided with direction members and screens.

16. The device according to claim 13, wherein said source of neutralizing electric charges is a corona type charge generator, which is provided with direction members and screens.

17. The device according to claim 13, wherein said source of neutralizing electric charges is an induction type charge generator, which is provided with direction members and screens.

18. The device according to claim 13, wherein said source of neutralizing electric charges is a tribo type charge generator, which is provided with direction members and screens.

19. The device according to claim 13, wherein said source of neutralizing electric charges continuously transmits neutralizing charges directed towards the multitude of charged particles deposited on the defined target area of said substrate member.

20. The device according to claim 13, wherein said source of neutralizing electric charges is located out of range of a dose forming area but in a position where said substrate and a dose being formed can be brought within range of emitted neutralizing charges by means of a servo device, such that the dose being formed is temporarily brought in position to get an accumulated electrostatic field neutralized at least once during forming of the dose.

21. A device for quick neutralization of a created electrostatic field formed by a multitude of basically charged particles comprising a medication powder deposited on a defined target area of a substrate member in a dose forming process, wherein an electric contact is established over an air gap between a non-contactable electrode behind said substrate member and a voltage source a source of electric charges is emitting sufficient charges into the air gap to convey an electric potential between the electrode and the voltage source with an impedance, inclusive of said air gap, less than 1 GΩ;

a controlled potential from said voltage source is connected through the air gap to the electrode thus creating a necessary electric field emanating from the electrode for transportation of charged particles to said defined target area of the dose forming process a source of neutralizing electric charges emitting positive or negative or both types of charges is provided within range of a dose being formed onto said defined target area of said substrate member;

said source of neutralizing electric charges transmitting neutralizing electric charges to a multitude of charged particles, deposited onto said defined target area of said substrate member, for the purpose of equalizing the charge in the dose being formed and also equalizing stray charges on the substrate surface, wherein said transmission of neutralizing electric charges is applied to a partial dose of said medication powder prior to subsequent deposition of further medication powder to complete said dose.

22. The device according to claim 21, wherein said voltage source has an impedance of less than 100 MΩ.

23. The device according to claim 21, wherein said source of electric neutralizing charges is an ion source which is provided with direction members and screens.

24. The device according to claim 21, wherein said source of electric neutralizing charges is a corona type charge generator.

25. The device according to claim 21, wherein said source of electric neutralizing charges is an induction type charge generator.

26. The device according to claim 21, wherein said source of electric neutralizing charges is a tribo type charge generator.

* * * * *